United States Patent
Robinson

(10) Patent No.: US 9,308,036 B2
(45) Date of Patent: Apr. 12, 2016

(54) PORTABLE ASSEMBLY AND METHOD FOR TREATING DESICCATED AND INJURED SPINAL DISCS

(71) Applicant: Ivan L. Robinson, Washington, DC (US)

(72) Inventor: Ivan L. Robinson, Washington, DC (US)

(*) Notice: Subject to any disclaimer, the term of this patent is extended or adjusted under 35 U.S.C. 154(b) by 327 days.

(21) Appl. No.: 14/075,238

(22) Filed: Nov. 8, 2013

(65) Prior Publication Data

US 2014/0214044 A1    Jul. 31, 2014

Related U.S. Application Data

(60) Provisional application No. 61/757,173, filed on Jan. 27, 2013.

(51) Int. Cl.
  *A61F 5/00* (2006.01)
  *A61B 17/88* (2006.01)
  *A61H 1/02* (2006.01)

(52) U.S. Cl.
  CPC ............ *A61B 17/885* (2013.01); *A61H 1/0222* (2013.01); *A61H 2201/1253* (2013.01); *A61H 2201/1436* (2013.01); *A61H 2201/1664* (2013.01); *A61H 2203/0456* (2013.01)

(58) Field of Classification Search
  CPC .......... A61G 1/00; A61G 1/04; A61G 1/044; A61G 2220/10; A61G 1/013; A61G 1/0293; A61G 2200/54; A61G 3/00; A61G 7/001; A61B 17/885; A61H 1/0218; A61H 1/0222; A61H 2201/1253; A61H 2201/1436; A61H 2201/1664; A61H 2203/0456
  USPC .............................. 602/19, 32–39; 5/627, 628
  See application file for complete search history.

(56) References Cited

U.S. PATENT DOCUMENTS

| | | | | |
|---|---|---|---|---|
| 951,515 A | * | 3/1910 | Solsem | A61H 1/0218 606/241 |
| 2,449,767 A | * | 9/1948 | Carpenter | A61G 1/00 5/627 |
| 3,413,971 A | * | 12/1968 | Evans | A61H 1/0218 602/32 |
| 3,426,367 A | * | 2/1969 | Bradford | A47C 17/645 403/108 |
| 3,811,433 A | * | 5/1974 | Brachet | A61G 1/00 5/628 |
| 6,994,683 B1 | | 2/2006 | Starr | |

OTHER PUBLICATIONS

Burton, C., Planet Earth and the Gravity of the Situation, The Burton Report, Web. Jan. 10, 2014 <http://www.burtonreport.com/InfSpine/ConservPlantErthGLR.htm>.

(Continued)

*Primary Examiner* — Michael Brown

(57) ABSTRACT

A portable assembly for treating desiccated and injured spinal discs includes a collapsible stretcher including a rectangular frame and a plurality of legs connected with the frame; a spinal stretching assembly connected with one end of the stretcher and an adjustable harness connected with the stretcher another end of the stretcher. The portable assembly operates to stretch and apply tension and decompression through the thoracic and lumbar regions of a patient lying on the stretcher. A method for treating desiccated and injured spinal discs includes the steps of administering at least one dietary supplement to the patient; administering at least one medication to the patient; hydrating the patient; positioning the patient on a stretcher in a prone position; stretching and applying tension and decompression through thoracic and lumbar regions of the patient via a spinal stretching assembly; and executing Chi breathing.

10 Claims, 4 Drawing Sheets

(56) References Cited

OTHER PUBLICATIONS

Ramos G., et al, Effects of Vertebral Axial Decompression on Intradiscal Pressure, J Neurosurg. Sep. 1994, pp. 350-353, 81(3).

Kirkaldy-Willis, et al, Gravity Lumbar Reduction, Managing Low Back Pain, 1983, pp. 191-197, Churchill Livingstone Inc., USA.
Spinal Stretch, Lowest-Cost Spinal Decompression, Web. Jan. 10, 2014 <http://spinalstretch.com/>.

* cited by examiner

PORTABLE ASSEMBLY AND METHOD FOR TREATING DESICCATED AND INJURED SPINAL DISCS

This application is a non-provisional application of U.S. provisional application No. 61/757,173 filed Jan. 27, 2013. The entire content of application No. 61/757,173 is incorporated herein by reference.

BACKGROUND OF THE INVENTION

This invention relates to treating disc injury without surgery, and more particularly, to a method for treating desiccated and injured thoracic through lumbar discs of the spine.

BRIEF DESCRIPTION OF THE PRIOR ART

Patients suffering back injuries are often informed of the need for immediate surgery with no guarantee of positive results. Nonsurgical methods of treating back injuries often utilize a combination approach of nutrition, Chiropractic and medical care.

Research by neurosurgeon Charles Burton, MD has shown that frequent stretching of the lower back (decompression) with a continuous pull of at least 25% of one's body weight has many beneficial effects including substantial pain relief, reducing "surgical candidate" need for surgery by 70%, potential regeneration of lumbar discs, and a patient satisfaction rate of 80%.

These nonsurgical methods require use of equipment that is not portable and easy to use for those desiring an active lifestyle. Further, these methods are not customizable to address individual patient needs.

The late William Kirkaldy-Willis, MD, editor of the textbook *Managing Low Back Pain*, is credited with discovering the "degenerative cascade," which offered the first comprehensive explanation of how the lumbar spine degenerates as a result of the cumulative effect of prolonged sitting which leads to dehydration and degeneration of the disc.

Disc dehydration can also lead to a wide range of painful aliments including sciatica, stenosis, muscle spasms, degenerative disc disease, pinched nerve roots, herniated discs, and facet syndrome (vertebrae jamming). In many cases, the cause of the pain is difficult to diagnose and the sufferer just knows that their back hurts.

The Starr U.S. Pat. No. 6,994,683 discloses a portable lumber traction device connected with a door frame. The device includes a belt which is secured around the waist of a patient, a cable including a tension spring and a ratcheting device. By activating the ratcheting device, the tension spring is increased and pressure is applied to a patient's spine.

While the Starr patent operates satisfactorily, the device cannot be used by military personnel in the field or people desiring active lifestyles. The device of the Starr patent is limited in that it is designed for indoor use.

The present invention was developed in order to overcome these limitations and other drawbacks of prior devices by providing an affordable, portable, easy to use, safe and effective device and method for treating desiccated and injured spinal discs in military personnel and others desiring an active lifestyle.

SUMMARY OF THE INVENTION

Accordingly, it is the primary object of the invention to provide a portable assembly for treating desiccated and injured spinal discs by administering a therapeutic decompressing force to increase the space between vertebrae, together with nutritional supplements, neurological degeneration inhibitors, analgesic pain relievers, hydration and Chi breathing to relieve thoracic and lumber pain, promote flexibility, and promote restorative disc healing by counteracting gravity.

The assembly includes a military style raised camping/medical utility stretcher, a harness connected with the stretcher, a spinal stretching assembly, and a fastener to removably connect the spinal stretching assembly to the stretcher. The spinal stretching assembly includes a tensioning assembly which is operated to draw the patient along the stretcher. The pulling force of the patient's body weight along the stretcher produces spinal decompression which counteracts gravity and increases the space between the vertebrae to bring relief to the thoracic through lumbar regions.

When it comes to back pain, few people understand the location of injury, degree of herniation resulting from a bulging disc, and the severity of desiccation. There are many causes of back pain, but the most common one is the force exerted by the earth's gravity. In fact, during every waking moment of a person's life the earth's gravity compresses the spine, particularly the sponge-like tissues known as spinal discs. The only time compression exerted by gravity is relaxed is during sleeping periods. During sleep, the spine is in a horizontal position that allows the spine the time to reclaim precious moisture that is depleted during standing and sitting activities of the day. Following decades of dehydration/rehydration, the compressive force of gravity results in thin, dry and brittle discs and a noticeably shorter stature in the elderly.

It is recommended that the portable assembly for treating desiccated and injured spinal discs be used approximately 15-20 minutes once or twice daily in conjunction with administration of nutritional supplements, neurological degeneration inhibitors, and analgesic pain relievers, a hydration plan and Chi abdominal breathing. Over time, and after having experienced a reduction in back pain, usage of the assembly may continue as a method of preventative care.

BRIEF DESCRIPTION OF THE FIGURES

Other objects and advantages of the invention will become apparent from a study of the following specification when viewed in light of the accompanying drawing, in which.

DETAILED DESCRIPTION

Figure 1:
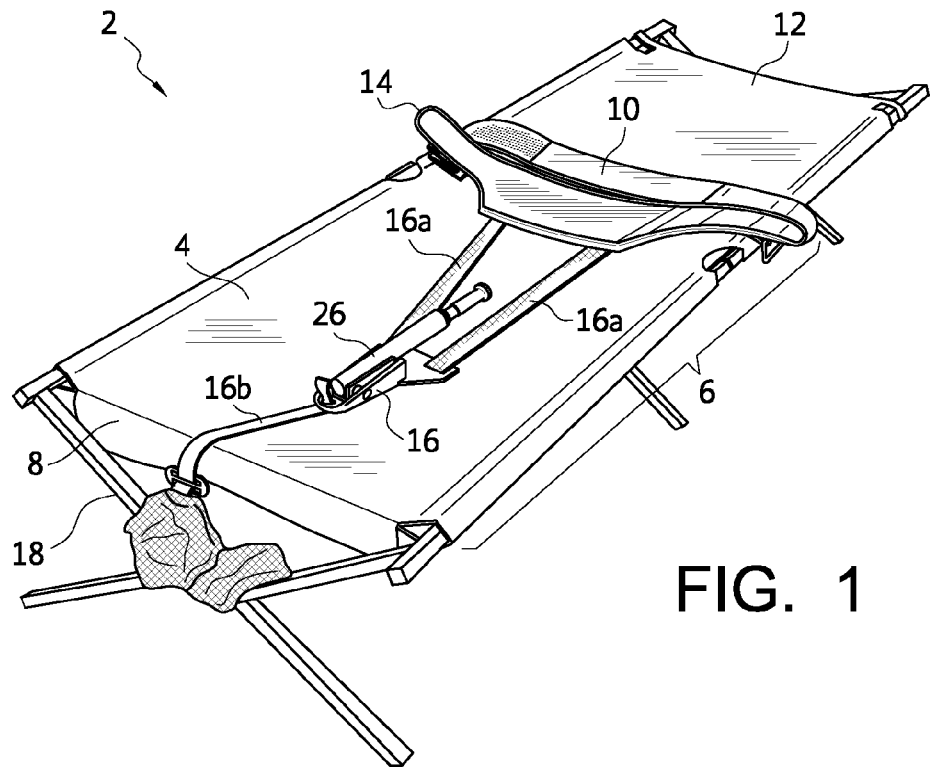
FIG. 1 is a perspective view of the portable assembly for treating spinal desiccated and injured discs.

FIG. 1 is a perspective view of a portable assembly 2 for treating spinal desiccated and injured discs and its component parts. Specifically, the portable assembly 2 includes a collapsible military style raised camping/medical utility stretcher 4, a spinal stretching assembly 6 connected with one end 8 of the stretcher 4 and an adjustable harness 10 connected with the stretcher in spaced relation with an opposite end 12 of the stretcher 4.

The spinal stretching assembly 6 includes an adjustable belt 14, a tensioning assembly 16, for example, a ratchet, and a telescoping handle 26 for operating the tensioning assembly. The tensioning assembly 16 further includes at least one fixed strap 16a and an adjustable strap 16b. A coupling device 22, such as an o-ring, is connected to the adjustable strap 16b.

Figure 2:
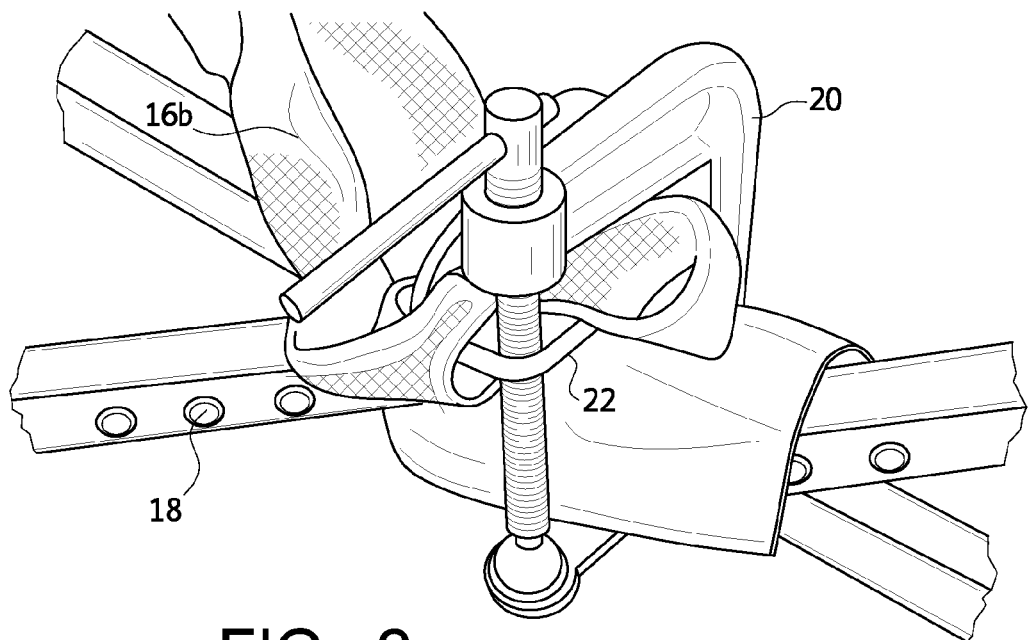
FIG. 2 is a side view of the fastening device and the connection between the spinal stretch assembly and the stretcher frame.

FIG. 2 is an end view of the stretcher frame 18 and the removable connection between the coupling device 22 of the adjustable strap 16b, the stretcher frame 18 and the fastening device 20. The spinal stretching assembly 6 must be disconnected from the stretcher frame 18 for storage and transport of the portable assembly 2.

Figure 3:
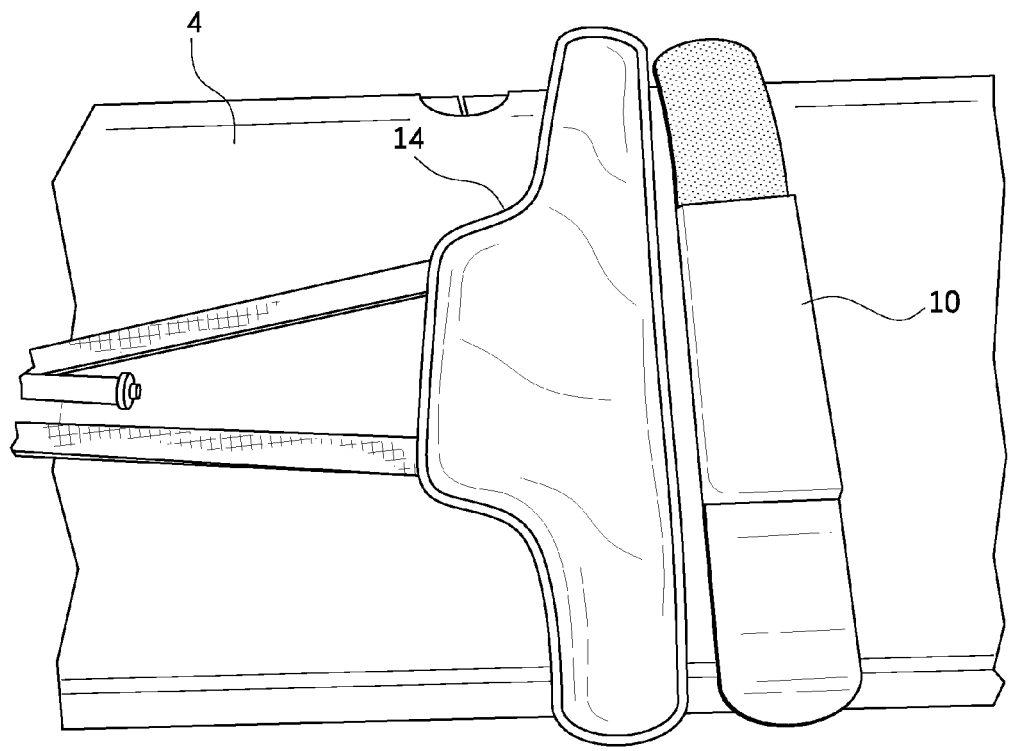
FIG. 3 is a top view of the stretcher, adjustable harness and spinal stretch assembly positioned on the stretcher.

Preferably, as shown in FIG. 3, the adjustable belt 14 of the spinal stretching assembly 6 is positioned approximately one inch below the harness 10 with the tensioning assembly 16 of the spinal stretching assembly 6 positioned away from the harness 10 and adjustable belt 14 toward the stretcher one end 8.

Figure 4:
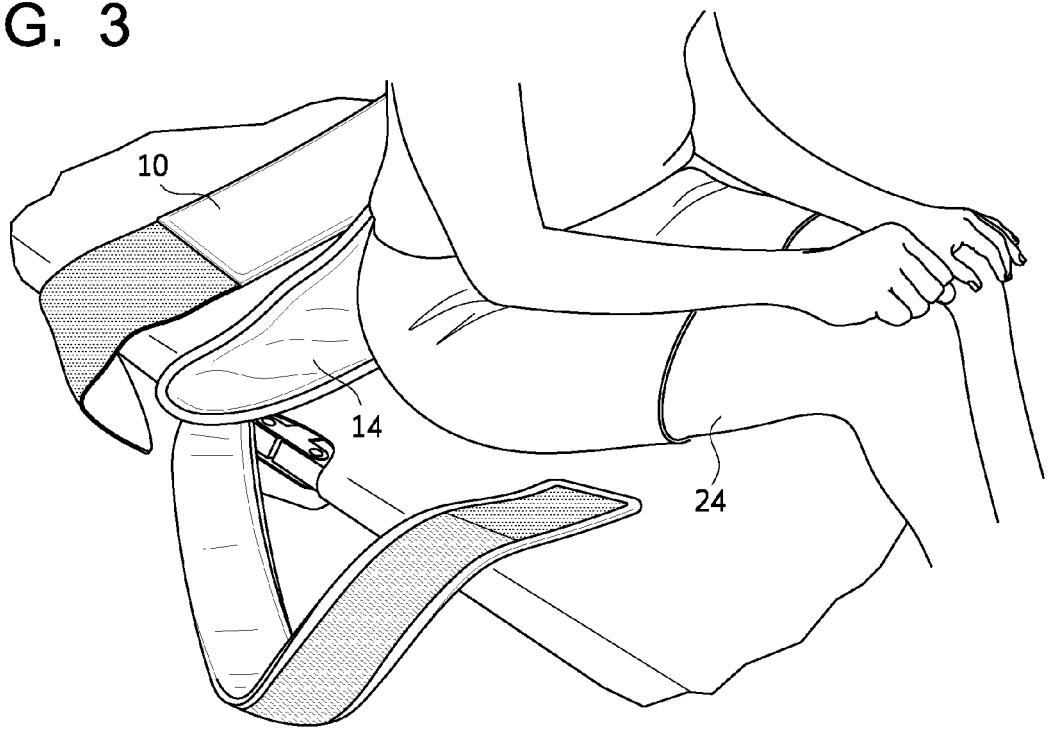
FIG. 4 is a perspective view of a patient seated on the stretcher and spinal stretch assembly according to the invention.

In an exemplary method as shown in FIG. 4, a patient 24 is oriented on the stretcher 4 and sits on the adjustable belt 14 of the spinal stretching assembly 6 with the feet extended toward the stretcher one end 8. The tensioning assembly 16 of the spinal stretching assembly 6 is placed between the patient's legs and the telescoping handle 26 of the tensioning assembly 16 is extended toward the patient's hands.

Figure 5:
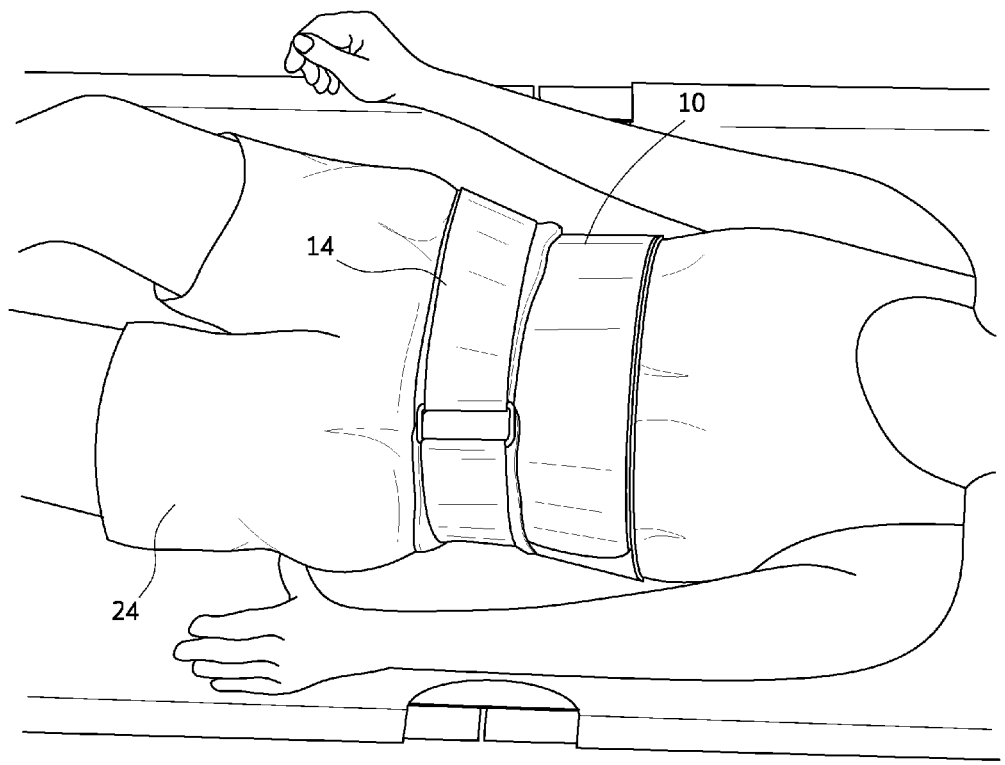
FIG. 5 is a top view of a patient lying on the stretcher with the harness and spinal stretch assembly belt connected around the patient.
Figure 6:
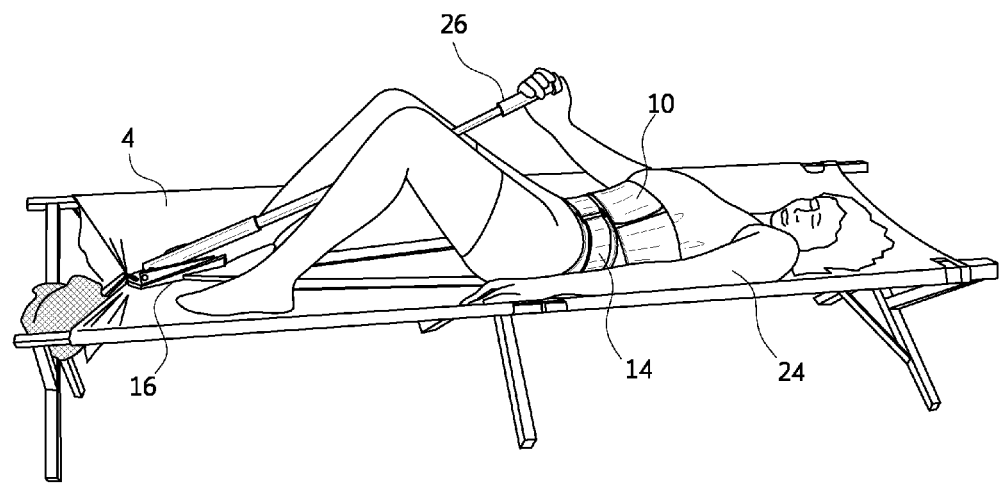
FIG. 6 is a side view of the portable assembly ready for operation by the patient.

In the exemplary method, as shown in FIGS. 5 and 6, the patient 24 lies upon the stretcher with the head in spaced relation with the stretcher opposite end 12. The adjustable harness 10 and adjustable belt 14 are then removably connected around the patient's 24 mid to upper thoracic region and lower pelvic region, respectively, of the patient's torso.

As shown in FIG. 6, the telescoping handle 26 is adjusted so that the patient may comfortably grasp the handle 26 when pulling on the handle 26 and applying tension to the tensioning assembly 16. The patient is then repositioned so that the knees are bent and the feet are flat on top of the stretcher 4.

When the tensioning assembly 16 of the spinal stretching assembly 6 is engaged, the friction force of the patient's 24 body weight, further restricted by the stretcher harness 10, along the surface of the stretcher 4 results in tension and decompression through the thoracic and lumbar regions of the patient 24 lying on the stretcher 4. As the application of the pulling force by the tensioning device 16 does not exceed 60-70% of the patient's body weight, there is little risk of injury. Further, any attempt to exceed a pulling force of 70% will exceed the friction force of the patient's body on the stretcher causing the patient to slide along the stretcher.

Figure 7:
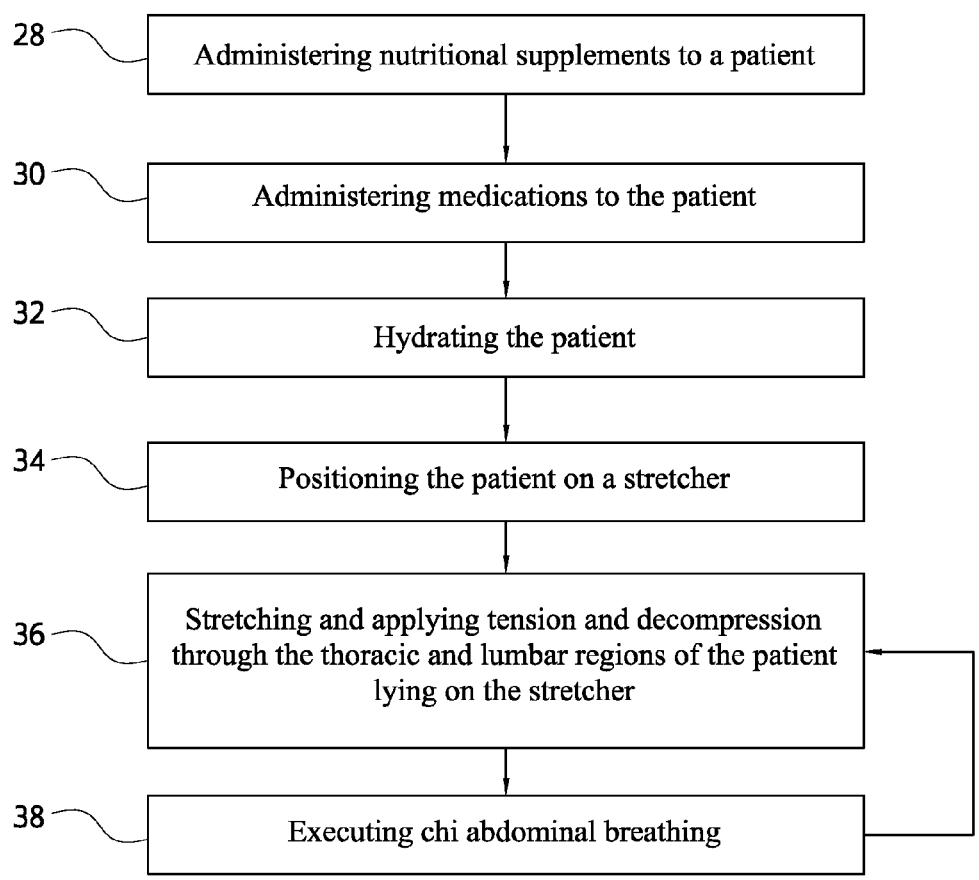
FIG. 7 is a flow diagram of an exemplary method for treating desiccated and injured spinal discs.

Referring now to FIG. 7, the method for treating desiccated and injured spinal discs according to the invention will be described. Initially, nutritional supplements are administered to the patient as shown by step 28. Next, medication is administered to the patient at step 30. Suitable medications include neurological degeneration inhibitors and analgesic pain relievers. The patient is sufficiently hydrated at step 32. Next, at step 34, the patient is positioned on a stretcher such as the portable assembly 2 shown in FIG. 1. The patient then operates the spinal stretching assembly 6 to stretch and apply tension and decompression through the thoracic and lumbar regions at step 36. During stretching, the patient executes chi abdominal breathing as shown at step 38. Use of the portable assembly 2 provides a safe, non-surgical, self-powered technique which stabilizes spinal injuries by eliminating nerve root impingement by providing disc decompression with pinpoint accuracy. Symptom relief is immediate, thereby allowing a patient to return to work and resume an active lifestyle as muscle strength, range of motion and flexibility are improved.

Use of the portable assembly is repeated once or twice daily over a 15-20 minute period. After pain has been reduced, daily use of the assembly can continue for preventative maintenance.

The supplements administration step 28 is performed twice daily and the supplements are selected from a group including at least one of vitamin B-complex, fish oil and glucosamine chondroitin.

The medication administering step 30 is repeated over a five day period and includes daily administration of neurological degeneration inhibitors selected from a group including at least one of 5 mg hydromorphone, 30 mg oxycodone, 5 mg dexamethasone and 10 mg dronabinol.

The medication administering step further includes the administration of an analgesic pain reliever twice daily over a fourteen day period. Such analgesic pain reliever may include 325 mg aspirin.

The hydration step 32 includes consuming 8 oz of water every hour while the patient is awake.

The key points to Chi cultivation are relaxation of all muscles by working with, not against gravity, mentally drawing energy from the earth, emptying the mind of all conscious thought, focusing the mind on the travel of the earth's energy though the body and delivery of the energy via breathing to and out of the extremities of the patient.

According to the inventive method, the patientlies on the stretcher in a relaxed state. With the mouth closed, the patient touches the roof of the mouth with the tongue. Breath is drawn into and out of the body naturally. The patient consciously relaxes each muscle and the mind is emptied of thought.

Chi is cultivated with circularity. Breath is slowly drawn into the body from the feet, following an imaginary light of energy. The light is drawn from the base of the feet into the ankles and up the legs, following the progression up the body and out the top of the head. On exhale, the light progresses from the top of the head, down the body and either exits the soles of the feet or exits at the point of pain. In the present invention, the pain is at the mid to upper thoracic region of a person's back.

While the preferred forms and embodiments have been illustrated and described, it will be apparent to those of ordinary skill in the art that various changes and modifications may be made without deviating from the inventive concepts set forth above.

What is claimed is:

1. A method for treating desiccated and injured spinal discs comprising the steps of
   (a) administering at least one dietary supplement to a patient;
   (b) administering at least one medication to the patient;
   (c) hydrating the patient;
   (d) positioning the patient on a stretcher in a supine position;
   (e) stretching and applying tension and decompression through thoracic and lumbar regions of the patient via a spinal stretching assembly; and
   (f) executing Chi abdominal breathing.

2. A method as defined in claim 1, wherein steps e and f are repeated over a 15-20 minute period.

3. A method as defined in claim 1, wherein said supplements administering step is performed twice a day and said supplements are selected from a group comprising at least one of vitamin B, fish oil, and glucosamine chondroitin.

4. A method as defined in claim 1, wherein said medication administering step comprises daily administration of neurological degeneration inhibitors selected from a group comprising at least one of hydromorphone, oxycodone, dexamethasone and dronabinol.

5. A method as defined in claim 4, wherein said medication administering step is repeated over a five day period.

6. A method as defined in claim 1, wherein said medication administering step further comprises administration of an analgesic pain reliever twice daily.

7. A method as defined in claim 6, wherein said medication administering step is repeated over a fourteen day period.

8. A method as defined in claim 1, wherein said hydration step comprises consumption of 8 oz of water every hour while the patient is awake.

9. A method as defined in claim 1, and further comprising the steps of:
(a) orienting a patient on the stretcher wherein the patient sits on an adjustable belt of the spinal stretching assembly with feet extended toward the stretcher opposite end;
(b) positioning a tensioning assembly of the spinal stretching assembly between the patient's legs;
(c) extending a telescoping handle of the tensioning assembly toward the patient's hands;
(d) repositioning patient on the stretcher, wherein the patient lies upon the stretcher with the head located in spaced relation with a first end of the stretcher;
(e) removably connecting the adjustable harness and the adjustable belt around the mid to upper thoracic portion and lower pelvic portion of the patient's torso, respectively;
(f) adjusting the telescoping handle so that the patient may grasp the telescoping handle; and
(g) repositioning patient so that the patient's knees are bent and the patient's feet are flat atop the stretcher.

10. A method as defined in claim 1, wherein said stretching step comprises slowly engaging a tensioning assembly of the spinal stretching assembly to stretch and apply tension and decompression through the thoracic and lumbar regions of a patient.

* * * * *